United States Patent
Chattaraj et al.

(10) Patent No.: US 9,642,810 B2
(45) Date of Patent: May 9, 2017

(54) FORMULATION CONTAINING CARBIDOPA, LEVODOPA, AND ENTACAPONE

(71) Applicant: MYLAN INC., Morgantown, WV (US)

(72) Inventors: Sarat C Chattaraj, Morgantown, WV (US); Kimberly S Moss, Morgantown, WV (US)

(73) Assignee: Mylan Inc., Canonsburg, PA (US)

( * ) Notice: Subject to any disclaimer, the term of this patent is extended or adjusted under 35 U.S.C. 154(b) by 20 days.

(21) Appl. No.: 14/774,975

(22) PCT Filed: Mar. 13, 2014

(86) PCT No.: PCT/US2014/026372
§ 371 (c)(1),
(2) Date: Sep. 11, 2015

(87) PCT Pub. No.: WO2014/151742
PCT Pub. Date: Sep. 25, 2014

(65) Prior Publication Data
US 2016/0022589 A1    Jan. 28, 2016

Related U.S. Application Data

(60) Provisional application No. 61/791,073, filed on Mar. 15, 2013.

(51) Int. Cl.
*A61K 31/198* (2006.01)
*A61K 9/16* (2006.01)
*A61K 9/20* (2006.01)
*A61K 31/277* (2006.01)

(52) U.S. Cl.
CPC .......... *A61K 9/2095* (2013.01); *A61K 9/1694* (2013.01); *A61K 9/2027* (2013.01); *A61K 9/2054* (2013.01); *A61K 9/2059* (2013.01); *A61K 31/198* (2013.01); *A61K 31/277* (2013.01)

(58) Field of Classification Search
None
See application file for complete search history.

(56) References Cited

U.S. PATENT DOCUMENTS

| | | |
|---|---|---|
| 9,370,577 B2 | 6/2016 | Goswami et al. |
| 2006/0222703 A1 | 10/2006 | Politi |
| 2009/0155369 A1 | 6/2009 | Huguet et al. |
| 2011/0091558 A1 | 4/2011 | Talwar |
| 2011/0229561 A1 * | 9/2011 | Kapoor ................ A61K 9/2027 424/452 |

FOREIGN PATENT DOCUMENTS

| | | |
|---|---|---|
| WO | 2010020969 A1 | 2/2010 |
| WO | 2010108845 A1 | 9/2010 |
| WO | 2011107653 A1 | 9/2011 |

OTHER PUBLICATIONS

"International Search Report for PCT/US2014/026372 dated Jun. 23, 2014".

* cited by examiner

*Primary Examiner* — Mary F Theisen

(57) ABSTRACT

Disclosed herein are stable pharmaceutical dosage forms containing carbidopa, levodopa, and entacapone. The dosage forms are prepared by mixing carbidopa, levodopa, and entacapone and forming granules. In some embodiments the granules also include starch. Microcrystalline cellulose can be added as an extragranular excipient. The stable pharmaceutical dosage forms have a bioavailability that is substantially similar to a dosage form prepared by adding a substantial portion of carbidopa separately from levodopa and entacapone.

19 Claims, 6 Drawing Sheets

US 9,642,810 B2

FORMULATION CONTAINING CARBIDOPA, LEVODOPA, AND ENTACAPONE

This application is a national stage filing under 35 U.S.C. §371 of PCT/US2014/26372, filed Mar. 13, 2014, which claims priority to U.S. Provisional Application No. 61/791,073, filed Mar. 15, 2013, the disclosures of which are incorporated by reference in their entirety herein.

BACKGROUND

1. Field of Art

Disclosed herein are solid fixed-dose pharmaceutical dosage forms that include carbidopa, levodopa, and entacapone, or their pharmaceutically acceptable salts, solvates, or hydrates thereof, and methods of preparing the pharmaceutical dosage forms. The dosage forms can be used, for example, in the treatment of Parkinson's disease.

2. Description of Related Art

Carbidopa, levodopa, and entacapone are therapeutic agents that are used to treat Parkinson's disease. Parkinson's disease is related to the depletion of dopamine. Levodopa (L-DOPA, or L-3,4-dihydroxyphenylalanine) is an aromatic amino acid derivative that is converted into dopamine in the body and increases dopamine levels. Unlike dopamine, levodopa is able to cross the blood-brain barrier. Therefore, administration of levodopa and its subsequent conversion to dopamine in the brain will increase dopamine levels in the brain. Administration of dopamine will not increase dopamine levels in the brain because dopamine does not cross the blood-brain barrier.

Carbidopa inhibits the decarboxylation of aromatic amino acids and inhibits the decarboxylation of levodopa into dopamine. Coadministration of carbidopa and levodopa results in increased plasma concentration of levodopa and improved efficacy. The uncarboxylated levodopa can be more readily absorbed into the brain and converted into dopamine. Coadministration of carbidopa and levodopa also increases the plasma half life of levodopa.

Entacapone is a peripherally acting selective and reversible inhibitor of catechol-O-methyltransferase (COMT). COMT metabolizes levodopa into 3-methoxy-4-hydroxy-L-phenylalanine. Therefore, administration of entacapone with levodopa prevents the degradation of levodopa and further increases its efficacy. When entacapone is dosed with carbidopa and levodopa the plasma levels of levodopa are greater and more sustained than administration of carbidopa and levodopa alone. The half life of levodopa is also increased. It is believed that increased plasma levels of levodopa leads to more constant dopaminergic stimulation in the brain and improved treatment of Parkinson's disease. As used herein, carbidopa, levodopa, and entacapone refer to the compounds as well as any salts, hydrates, or solvates thereof.

Due to the relationship between levodopa, carbidopa, and entacapone they are often dosed together. For example, the commercially available dosage forms PARCOPA® and SINEMET® include carbidopa and levodopa, while the dosage form COMTAN® includes entacapone. Each of the dosage forms are used to treat Parkinson's disease. The commercially available dosage form STALEVO® contains all three compounds in one dosage form and is used to treat Parkinson's disease.

STALEVO® is a replacement for individual carbidopa/levodopa and entacapone products and is described by U.S. Pat. No. 6,500,867 ("the '867 patent"). The '867 patent discloses a single dosage form that includes each of carbidopa, levodopa, and entacapone. According to the specification, the bioavailability of the dosage form is increased when a substantial portion of carbidopa is added separately to levodopa and entacapone. The carbidopa can be added to the formulations of the '867 patent as granules or as a powder that is distinct from the granules or powder containing levodopa and entacapone. A substantial portion of the carbidopa is separated from the entacapone and levodopa when levodopa and entacapone are mixed separately and then carbidopa is added to the mixture of levodopa and entacapone.

The '867 patent teaches that microcrystalline cellulose should not be used as an excipient. According to Example 1 of the '867 patent, when a formulation is prepared by wet granulating carbidopa, levodopa, and entacapone together and adding microcrystalline cellulose the bioavailability of the resulting composition is lower than pharmaceutically acceptable. An acceptable bioavailability may be 80-125% of the bioavailability of STALEVO® for a given pharmacokinetic parameter, such as AUCL or CPEAK. A different formulation can be prepared by dry granulating carbidopa, levodopa, and entacapone. However, the dry granulated formulation is unstable when microcrystalline cellulose is used as an excipient. According to the specification, microcrystalline cellulose destabilizes carbidopa/levodopa/entacapone compositions that contain all three compounds when the formulation is stored for a long term.

U.S. Published Patent Application No. 2006/0222703 ("the '703 publication") also discloses a formulation that includes each of carbidopa, levodopa, and entacapone. However, the formulation is prepared using a "solvent free" method of mixing the compounds. According to the '703 publication wet granulating levodopa, carbidopa, and entacapone leads to unacceptable stability of the resulting dosage form. The document states that a wet granulated dosage form containing carbidopa, levodopa, and entacapone is unacceptably large in size. PCT Publication No. WO 2009/098661 discloses a formulation containing each of carbidopa, levodopa, and entacapone where the entacapone is added to the formulation by comicronizing entacapone with a sugar alcohol.

None of the formulations discussed above are prepared by wet granulation of a mixture of carbidopa, levodopa, and entacapone together, resulting in a stable composition with a pharmaceutically acceptable bioavailability. Therefore, there is a need for a stable pharmaceutical composition that is prepared by wet granulation of carbidopa, levodopa, and entacapone, wherein the compounds are mixed together before incorporation into the dosage form.

SUMMARY

In light of the present need for a dosage form containing a mixture of carbidopa, levodopa, and entacapone, a brief summary of various embodiments is presented. Some simplifications and omissions may be made in the following summary, which is intended to highlight and introduce some aspects of the various embodiments, but not to limit the scope of the stable pharmaceutical dosage forms described herein. Detailed descriptions of some embodiments adequate to allow those of ordinary skill in the art to make and use the concepts will follow in later sections.

The stable pharmaceutical dosage form described herein includes granules containing a mixture of carbidopa, levodopa, and entacapone or pharmaceutically acceptable salts, solvates, or hydrates thereof. The granules may also include at least one optional first excipient. The granules containing carbidopa, levodopa, and entacapone may then be mixed with at least one second excipient and compressed into a tablet.

The process for preparing the stable pharmaceutical dosage form includes the steps of mixing carbidopa, levodopa, and entacapone to form a mixture. The mixture is then wet-granulated with a granulation solution to form a granulation mixture. The granulation mixture is dried to form dried granules that contain carbidopa, levodopa, and entacapone. The dried granules of carbidopa, levodopa, and entacapone are mixed with at least one excipient to form a second mixture. The second mixture is compressed into a stable pharmaceutical dosage form.

The stable pharmaceutical dosage form may include at least one excipient in addition to the mixture of carbidopa, levodopa, and entacapone. The at least one excipient may be added to the mixture of carbidopa, levodopa, and entacapone prior to wet granulation or the at least one excipient may be mixed with the dried granules prior to step of compressing the dried granules into a stable pharmaceutical dosage form. The stable pharmaceutical dosage form described herein may also include at least one first excipient added to the mixture of carbidopa, levodopa, and entacapone prior to the granulation step as well as at least one second excipient mixed with the dried granules prior to the step of compressing into a stable pharmaceutical dosage form. The at least one first excipient may be the same or different from the at least one second excipient.

An example of the at least one excipient that is added to the mixture of carbidopa, levodopa, and entacapone prior to granulation is starch. When starch is added to the mixture of carbidopa, levodopa, and entacapone the mixture is used in the wet granulation step of preparing the stable pharmaceutical dosage form. Therefore, the granulation mixture will contain starch in addition to carbidopa, levodopa, and entacapone. The dried granules will also contain starch in addition to carbidopa, levodopa, and entacapone. Thus starch can be incorporated into the granules of carbidopa, levodopa, and entacapone and into the stable pharmaceutical dosage form by adding starch to the mixture of carbidopa, levodopa, and entacapone prior to wet granulation.

An example of the at least one excipient that is mixed with the granules of carbidopa, levodopa, and entacapone is microcrystalline cellulose. Microcrystalline cellulose can be added to dried granules of carbidopa, levodopa, and entacapone that do not contain starch or microcrystalline cellulose can be added to dried granules of carbidopa, levodopa, entacapone, and starch.

DETAILED DESCRIPTION

Figure 1:
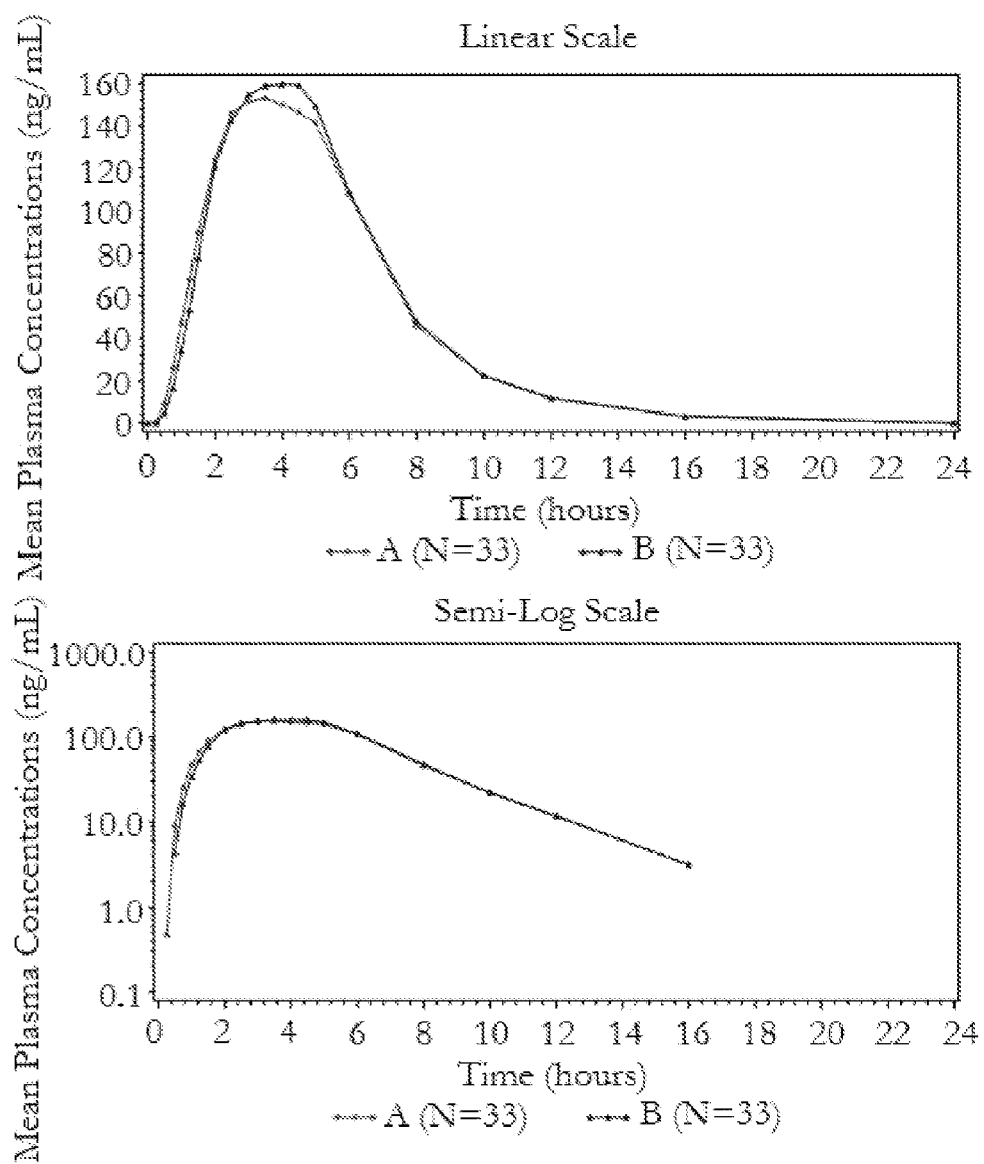
FIG. 1 shows the linear and semi-logarithmic comparison of the mean plasma concentration of carbidopa over time following administration of a stable dosage form that includes 50 mg carbidopa/200 mg levodopa/200 mg entacapone as compared to STALEVO®.
Figure 2:
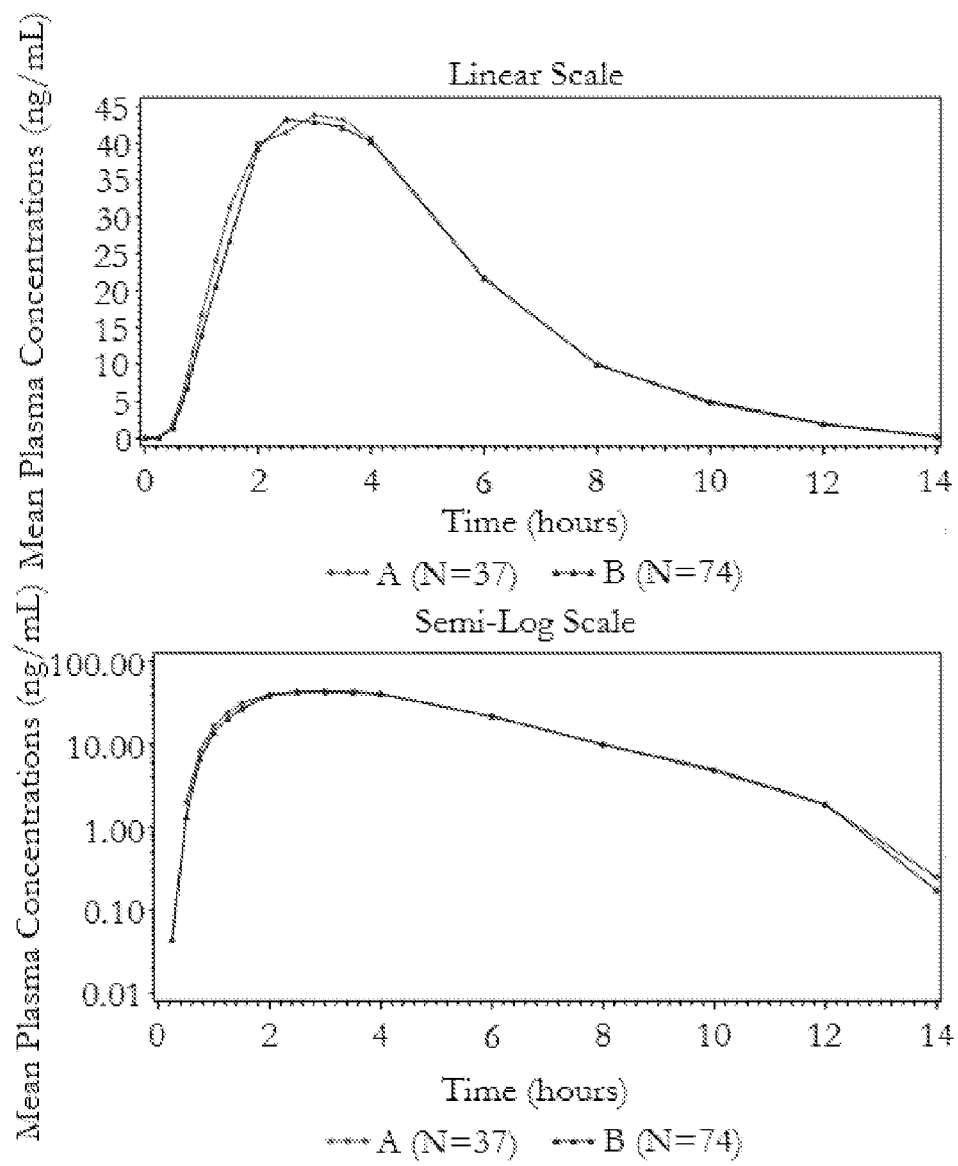
FIG. 2 shows the linear and semi-logarithmic comparison of the mean plasma concentration of carbidopa over time following administration of a stable dosage form that includes 12.5 mg carbidopa/50 mg levodopa/200 mg entacapone as compared to STALEVO®.
Figure 3:
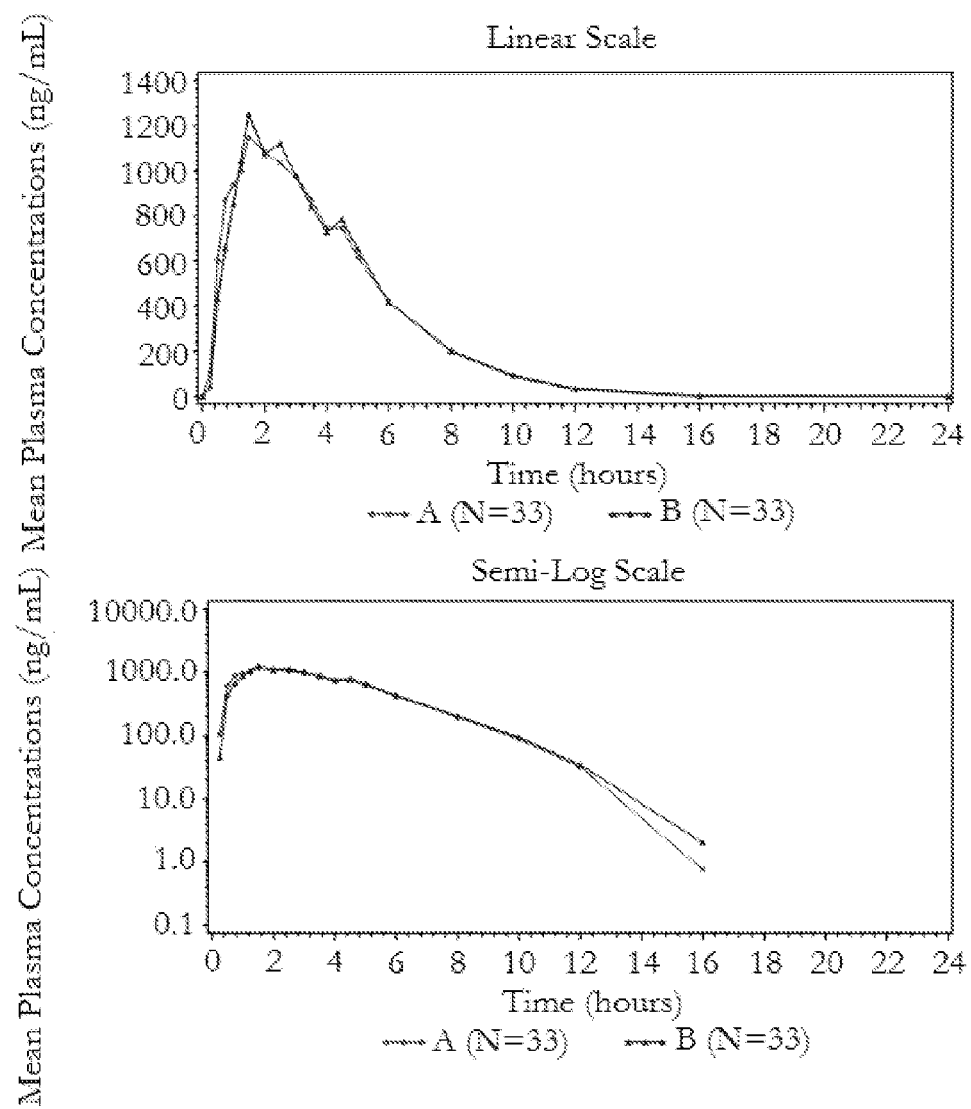
FIG. 3 shows the linear and semi-logarithmic comparison of the mean plasma concentration of levodopa over time following administration of a stable dosage form that includes 50 mg carbidopa/200 mg levodopa/200 mg entacapone as compared to STAVELO®.
Figure 4:
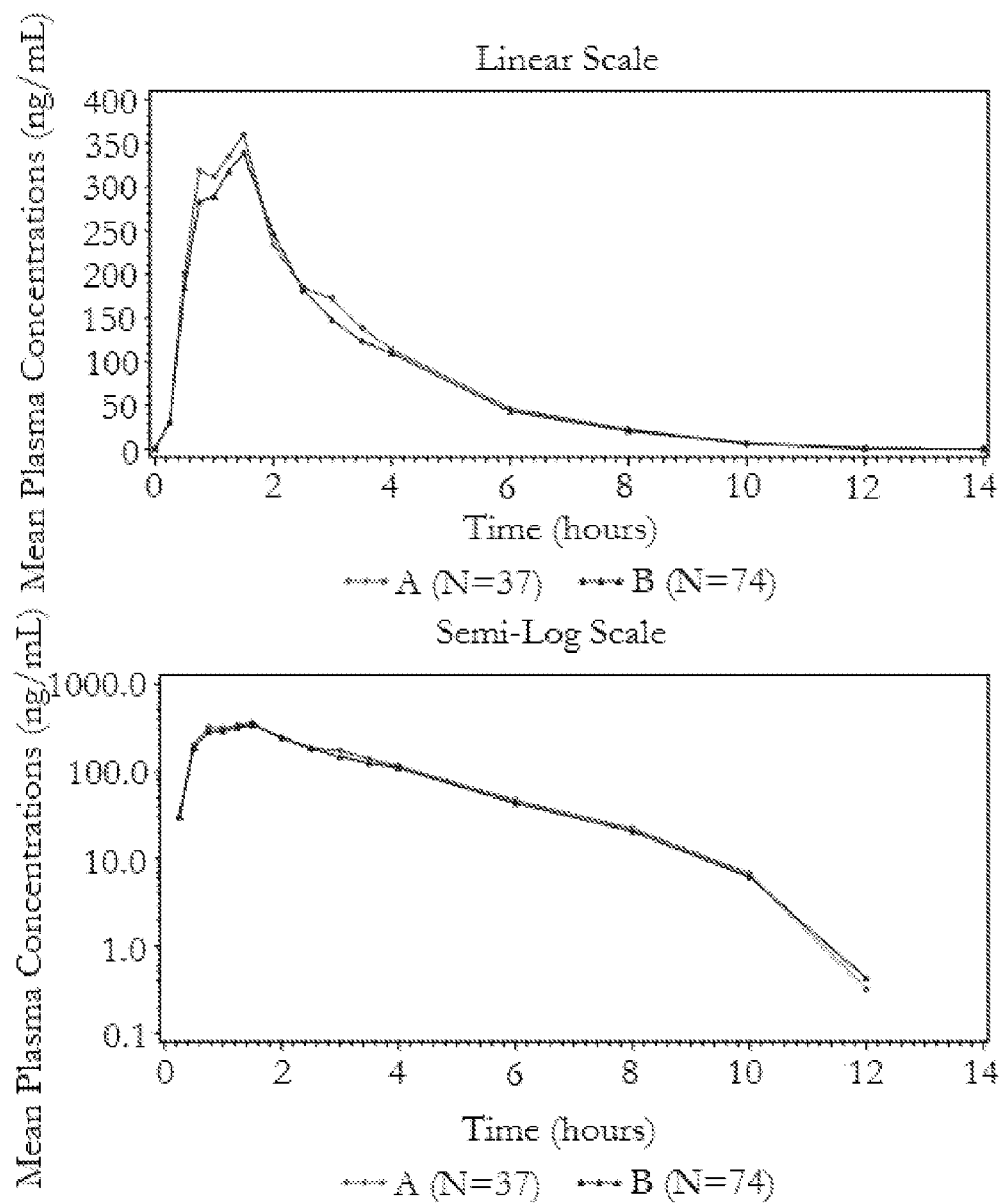
FIG. 4 shows the linear and semi-logarithmic comparison of the mean plasma concentration of levodopa over time following administration of a stable dosage form that includes 12.5 mg carbidopa/50 mg levodopa/200 mg entacapone as compared to STALEVO®.
Figure 5:
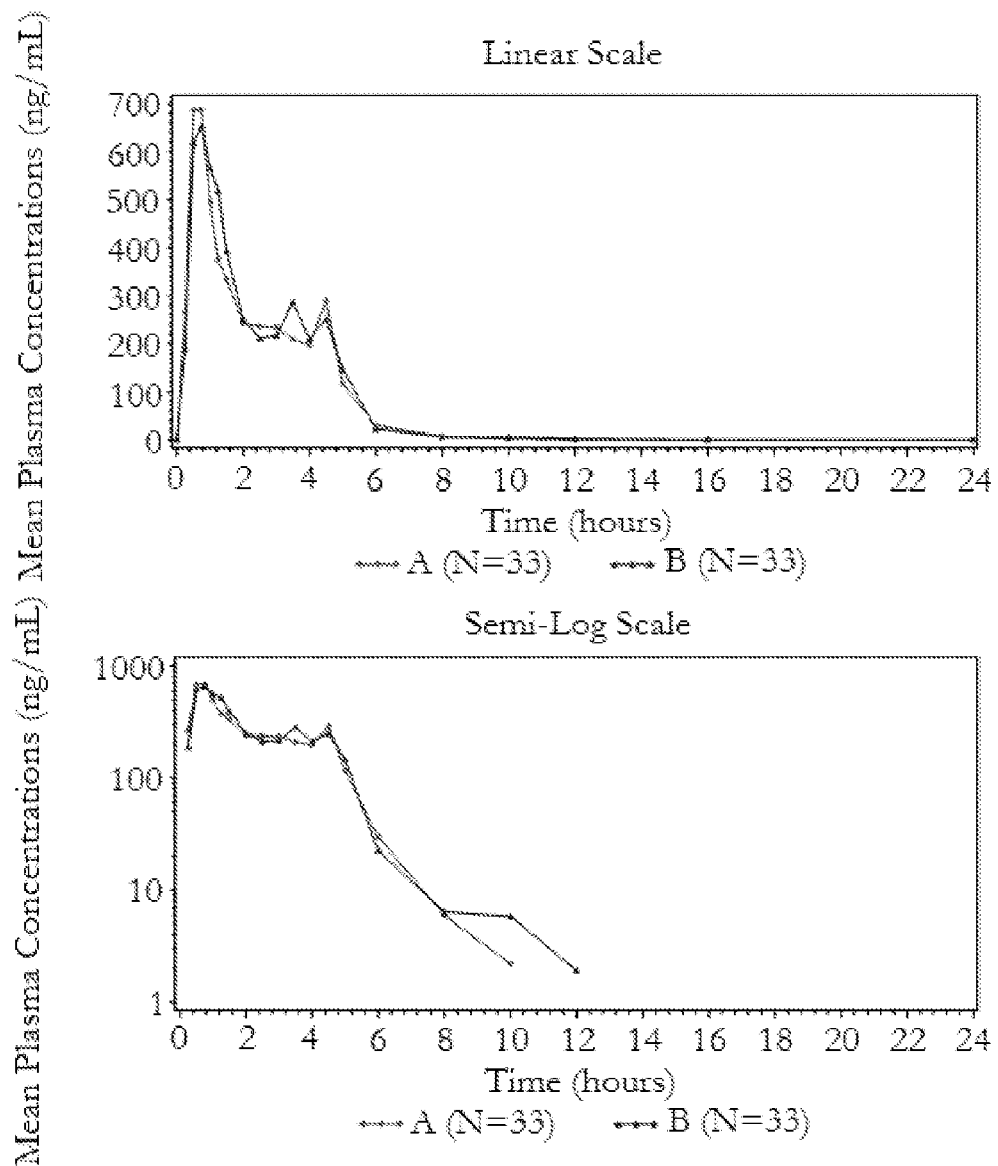
FIG. 5 shows the linear and semi-logarithmic comparison of the mean plasma concentration of entacapone over time following administration of a stable dosage form that includes 50 mg carbidopa/200 mg levodopa/200 mg entacapone as compared to STALEVO®.
Figure 6:
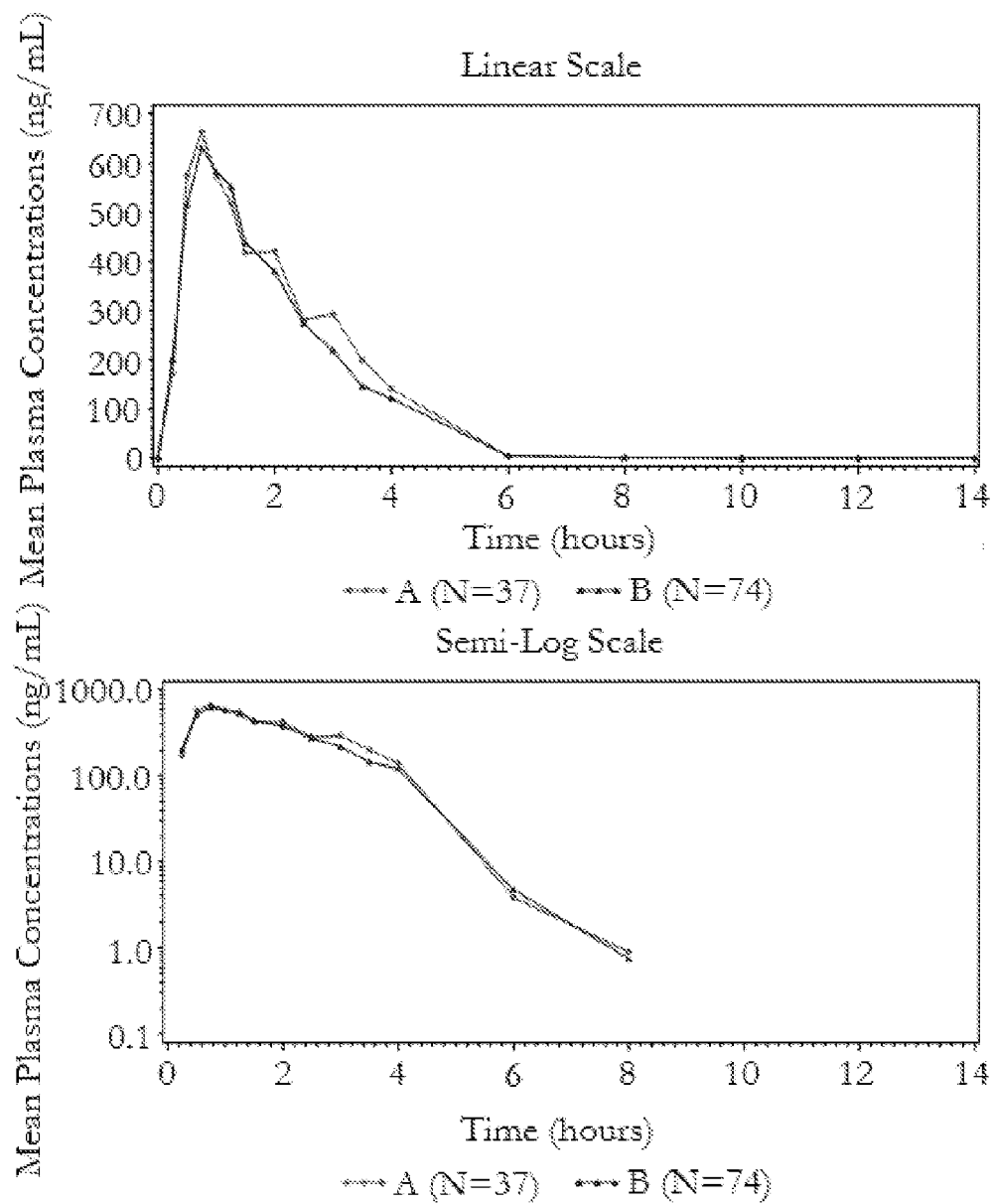
FIG. 6 shows the linear and semi-logarithmic comparison of the mean plasma concentration of entacapone over time following administration of a stable dosage form that includes 12.5 mg carbidopa/50 mg levodopa/200 mg entacapone as compared to STALEVO.

The stable pharmaceutical dosage form described herein can be prepared by wet granulation. The first step of the wet granulation process includes mixing or blending carbidopa, levodopa, and entacapone, or their pharmaceutically acceptable salts, solvates or hydrates thereof, to form a mixture. The step of mixing or blending can be performed in a high shear granulating bowl. The mixture may then be granulated with a granulating solution to form a granulation mixture. The granulating solution may be an aqueous solution, an alcohol solution, or a water and alcohol solution containing a water-soluble or water-dispersible polymeric material. The water-soluble or water-dispersible polymeric material may be a pharmaceutically acceptable cellulosic polymer or a pharmaceutically acceptable vinyl polymer. In various embodiments, the granulating solution may be an aqueous solution of a cellulosic binder. An example of an acceptable cellulosic binder used in the granulation solution is hydroxypropyl cellulose. However, other granulation solutions containing different solvents or different binders may be used to prepare the stable pharmaceutical dosage form. Non-aqueous granulation solvents, such as alcohol solvents, may be used to prepare the granules. In addition, non-cellulosic binders, such as povidone, or additional cellulosic binders, such as carboxymethyl cellulose, may be used to form the granules. Following granulation with the granulation solution the wet granulation mixture can be dried in a fluid bed to form dried granules. The dried granules prepared from the granulation mixture may then be milled and compressed into a stable pharmaceutical dosage form. One example of a stable pharmaceutical dosage form prepared by this process is a tablet.

In one embodiment of the stable pharmaceutical dosage form, starch is mixed with the carbidopa, levodopa, and entacapone prior to granulation with the granulation solution. The starch used in the stable pharmaceutical dosage form may be pregelatinized starch, corn starch, or a mixture thereof. Other types of pharmaceutically acceptable starches may also be used to prepare the stable pharmaceutical dosage form. After mixing starch with the carbidopa, levodopa, and entacapone, the mixture is granulated with the granulation solution as described above to prepare a granulation mixture containing carbidopa, levodopa, entacapone, and starch. The granulation mixture is dried to form granules containing carbidopa, levodopa, entacapone, and starch, milled, and compressed as described above.

Microcrystalline cellulose may be added to the stable pharmaceutical dosage form as an extragranular excipient. Following preparation of granules containing carbidopa, levodopa, and entacapone, and optionally containing starch, microcrystalline cellulose may be blended with the dried and milled granules. Any pharmaceutically acceptable amount of microcrystalline cellulose may be mixed with the granules as long as the resulting pharmaceutical dosage form is stable. In one embodiment, microcrystalline cellulose is added to the stable pharmaceutical dosage form in an amount of about 12% to about 22% by weight of the total weight of the pharmaceutical dosage form. In another embodiment, microcrystalline cellulose is added in amount of about 17% by weight of the total weight of the stable pharmaceutical dosage form. Any pharmaceutically acceptable form of microcrystalline cellulose may be used in the stable pharmaceutical dosage form. One example of a form of microcrystalline cellulose that may be used in the stable pharmaceutical dosage form is Avicel PH 102.

Other extragranular excipients may be added to the stable pharmaceutical dosage form. Examples of other excipients include fillers, binders, disintegrants, and lubricants. One example of a disintegrant used in the stable pharmaceutical dosage form is crospovidone. Another example of a disintegrant is croscarmellose sodium. The lubricant may be magnesium stearate. The addition of other excipients may not affect the stability or bioavailability of the stable pharmaceutical dosage form.

Following the preparation of granules, the optional addition of excipients, and the compression of the mixture, the stable pharmaceutical dosage form may be coated. The coating may be a color coat, a clear coat, or a mixture thereof. The stable pharmaceutical dosage form described herein exhibits an immediate release of carbidopa, levodopa, and entacapone.

The stable pharmaceutical dosage form may include an effective amount of each of entacapone, carbidopa, and levodopa as known to a person of skill in the art. In one embodiment, the stable pharmaceutical dosage form may include about 25-400 mg of entacapone, preferably about 25-300 mg, and more preferably about 50-200 mg. In another embodiment, the stable pharmaceutical dosage form may include about 25-300 mg of levodopa, preferably about 50-250 mg. In yet another embodiment, the stable pharmaceutical dosage form may include about 5-75 mg of carbidopa, preferably about 10-50 mg. A particularly preferred embodiment of the stable pharmaceutical dosage form includes 200 mg of entacapone, 100 mg of levodopa, and 25 mg carbidopa. Other preferred embodiments include 200 mg of entacapone, 50 mg of levodopa, and 12.5 mg carbidopa; 200 mg of entacapone, 150 mg of levodopa, and 37.5 mg of carbidopa; 200 mg of entacapone, 100 mg of levodopa, and 10 mg of carbidopa; 200 mg of entacapone, 250 mg of levodopa, and 25 mg of carbidopa; 200 mg of entacapone, 75 mg of levodopa, and 18.75 mg of carbidopa; and 200 mg of entacapone, 125 mg of levodopa, and 31.25 mg of entacapone.

The stable pharmaceutical dosage form can be used to treat Parkinson's disease in the different stages of the disease. The stable pharmaceutical dosage form used to treat Parkinson's disease can include the amounts of carbidopa, levodopa, and entacapone described above. The stable pharmaceutical dosage form used to treat Parkinson's disease can also includes salts, hydrates, and solvates of carbidopa, levodopa, or entacapone.

As discussed above, the pharmaceutical dosage form is stable. The '867 patent teaches that wet granulated dosage forms containing carbidopa, levodopa, and entacapone and microcrystalline cellulose are not stable. However, the pharmaceutical dosage form described herein, which may be prepared by wet granulation and which may include microcrystalline cellulose, show acceptable stability.

Stability may be determined by storing the stable pharmaceutical dosage form under acceptable storage conditions and monitoring the appearance of impurities over time. One example of an acceptable storage condition used to determine stability is a temperature of 40° C. and a relative humidity of 75%. The stability of the pharmaceutical dosage form may be determined by first recording the amount of particular impurities by weight as compared to the total weight of the stable pharmaceutical dosage form. Impurities may result from the degradation of carbidopa, levodopa, and entacapone by hydrolysis and/or oxidation. The amount of the particular impurity may then be measured again at specified time intervals. The stable pharmaceutical dosage forms described herein will have no more than acceptable levels of particular impurities at the specified time intervals. Acceptable impurity levels of compounds derived from carbidopa and/or entacapone include less than about 0.50%, preferably less than about 0.25% of methyl-Dopa; less than about 0.40%, preferably less than about 0.20% of 3,4-Dihydroxyphenylacetone; or less than about 0.05% of other compounds derived from carbidopa and/or levodopa, by weight. Additional acceptable impurities derived from entacapone may be present at less than about 0.05% by weight.

In addition to the stability discussed above the stable pharmaceutical dosage form exhibits an acceptable bioavailability. The bioavailability may be substantially similar to a reference dosage form containing carbidopa, levodopa, and entacapone that is prepared by separating a substantial portion of the carbidopa from the entacapone and levodopa. One example of a reference dosage form is the commercially available carbidopa, levodopa, and entacapone dosage form STALEVO®. Other reference dosage forms include carbidopa, levodopa, and entacapone in one dosage form, such as those described in U.S. Pat. No. 6,500,867. The reference dosage form does not include microcrystalline cellulose and is not prepared by wet granulation.

The stable pharmaceutical dosage form described herein has an acceptable bioavailability that is substantially similar to a reference dosage form despite the fact that the stable pharmaceutical dosage form described herein may be prepared by wet granulation and may include microcrystalline cellulose. The stable pharmaceutical dosage form described herein also does not require separating a substantial portion of carbidopa from entacapone and levodopa, which is required in the reference dosage form.

EXAMPLE 1

Process for Preparing a Stable Pharmaceutical Dosage Form

Purified water is added to a stainless steel container. Hydroxypropyl cellulose is added to the purified water with continuous mixing and mixed for minimum of 30 minutes. One-half of the dose of entacapone, the entire dose of carbidopa, the entire dose of levodopa, the remaining one-half of the dose of entacapone, pregelatinized starch, and corn starch are added to the bowl of a high shear mixer granulator and dry mixed for three minutes. The hydroxypropyl cellulose solution is used to granulate the mixture to produce granules. The granules are dried in a fluid bed drier and milled in a Fitz mill.

The milled granules are then added to a blender. Microcrystalline cellulose and crospovidone are added to the blender and the mixture is blended for 10 minutes. Magnesium stearate is added to the mixture and blended for an additional five minutes. The mixture is compressed into tablets and coated with a clear coating and a color coating.

The stable pharmaceutical dosage form was prepared using the indicated amounts of carbidopa, levodopa, and entacapone and excipients:

TABLE 1

| Component | 12.5/50/200 mg mg/tablet | 18.75/75/200 mg mg/tablet | 25/100/200 mg mg/tablet | 31.25/125/200 mg mg/tablet | 37.5/150/200 mg mg/tablet | 50/200/200 mg mg/tablet |
|---|---|---|---|---|---|---|
| Hydroxypropyl Cellulose (Klucel EF) | 6.6 | 7.47 | 8.58 | 9.1 | 10.53 | 11.73 |
| Purified Water | (63.8) | (72.2) | (82.9) | (88.0) | (101.8) | (113.4) |
| Carbidopa | 13.5 | 20.25 | 27.00 | 33.75 | 40.5 | 54 |
| Levodopa | 50.00 | 75.00 | 100.00 | 125.0 | 150.0 | 200 |
| Entacapone | 200.00 | 200.00 | 200.00 | 200.00 | 200.00 | 200 |
| Pregelatinized Starch (Starch 1500) | 39.03 | 44.18 | 50.76 | 53.7 | 62.3 | 67.15 |
| Corn Starch, NF | 26.97 | 30.48 | 35.04 | 37.05 | 43.0 | 45.7 |
| Microcrystalline Cellulose (Avicel PH 102) | 77.5 | 93.24 | 119.16 | 113.12 | 157.06 | 159.46 |
| Crospovidone (Polyplasdone XL) | 17.6 | 20.15 | 22.88 | 24.2 | 28.08 | 31.24 |
| Magnesium Stearate | 8.8 | 7.23 | 8.58 | 9.08 | 10.53 | 11.72 |
| Total Core Weight | 440.0 | 498.0 | 572.0 | 605.0 | 702.0 | 781.0 |
| Purple Opadry II (40C100000) | N/A | 17.4 | 20.0 | N/A | N/A | 27.0 |
| Purple Opadry II (40C100000) | 15.4 | N/A | N/A | 21.2 | 24.6 | N/A |
| Clear Opadry (YS-1-7006) | 1.1 | 1.2 | 1.4 | 1.5 | 1.8 | 2.0 |
| Total Coated Weight | 456.50 | 516.60 | 593.40 | 627.70 | 728.40 | 810.0 |

EXAMPLE 2

Stability Data for the Stable Pharmaceutical Dosage Form

Tablets prepared according to the process of Example 1 were stored at 40° C. and 75% relative humidity. The tablets included 50 mg of carbidopa, 200 mg of levodopa, and 200 mg of entacapone. 100 count bottles and 500 count bottles were stored and sampled for impurity content. Impurity levels were measured by HPLC, however, impurities can be measured by any other standard measurement technique known to a person of skill in the art. The amount of impurities were measured over the course of 4 weeks, 8 weeks, and 12 weeks, and the results are show in Table 1 below:

TABLE 2

| | | Carbidopa and levodopa derived impurities (% by weight) | | | | Entacapone derived impurities (% by weight) | | | | | |
|---|---|---|---|---|---|---|---|---|---|---|---|
| | | Methyl Dopa | 3,4-DHPA | Unknown Impurity | Total Imp | Imp-A | Imp-B | Imp-C | Imp-H | Unknown Impurity | Total Impurities |
| Initial amount | | 0.22 | 0.13 | LT 0.05 | 0.22 | LT 0.05 | LT 0.05 | LT 0.05 | LT 0.05 | 0.06 | 0.06 |
| | | | | 100 count bottles | | | | | | | |
| 4 weeks | | 0.22 | 0.19 | LT 0.05 | 0.22 | LT 0.05 | LT 0.05 | LT 0.05 | LT 0.05 | 0.06 | 0.12 |
| 8 weeks | | 0.23 | 0.23 | LT 0.05 | 0.23 | LT 0.05 | LT 0.05 | LT 0.05 | LT 0.05 | 0.06 | 0.06 |
| 12 weeks | | 0.24 | 0.27 | LT 0.05 | 0.24 | LT 0.05 | LT 0.05 | LT 0.05 | LT 0.05 | LT 0.05 | LT 0.05 |
| | | | | 500 count bottles | | | | | | | |
| 4 weeks | | 0.22 | 0.19 | LT 0.05 | LT 0.50 | LT 0.05 | LT 0.05 | LT 0.05 | LT 0.05 | 0.06 | 0.12 |
| 8 weeks | | 0.23 | 0.22 | LT 0.05 | 0.23 | LT 0.05 | LT 0.05 | LT 0.05 | LT 0.05 | 0.06 | 0.06 |
| 12 weeks | | 0.24 | 0.25 | LT 0.05 | 0.24 | LT 0.05 | LT 0.05 | LT 0.05 | LT 0.05 | LT 0.05 | LT 0.06 |

The carbidopa- and levodopa-derived impurities include methyl-Dopa (L-tyrosine, 3-hydroxy-α-methyl-, sesquihydrate), 3,4-dihydroxyphenylacetone (3,4-DHPA), and other unknown impurities derived from carbidopa and/or levodopa. The entacapone-derived impurities include 3,4-dihydroxy-5-nitrobenzaldehyde ("Imp-A"), N,N'-diethyl-2-cyanoacetamide ("Imp-B"), 3,4-dihydroxy-5-nitrobenzoic acid ("Imp-C"), (Z)-2-cyano-3-(3,4-dihydroxy-5-nitrobenzoic acid ("Imp-H"), and other unknown impurities derived from entacapone.

EXAMPLE 3

Bioavailability of the Stable Pharmaceutical Dosage Form

The following bioavailability data were obtained by administering the stable pharmaceutical dosage form of Example 1 to healthy volunteers in two fasting studies. The data show the pharmacokinetic parameters, with the indicated coefficients of variation for the 50 mg carbidopa/200 mg levodopa/200 mg entacapone dosage form, derived from administration of the stable pharmaceutical dosage form as compared to the administration of STALEVO® with the indicated amounts of carbidopa, levodopa, and entacapone, respectively:

The parameter AUCL is the area under the plasma concentration-time curve from time zero to time t, where t is the last time point with measurable concentration for individual formulation. CPEAK is the maximum plasma concentration of the drug and TPEAK is the time until the maximum plasma concentration is reached. The pharmacokinetic parameters including AUCL, CPEAK, and TPEAK are within about 80% to about 125% of the same pharmacokinetic parameters of the reference dosage form.

The standards for bioequivalence depend on several natural log transformed parameters associated with the rate and extent of absorption. Specifically, bioequivalence depends on the parameters including AUCL and CPEAK and other pharmacokinetic parameters such as AUCinf. According to FDA guidelines, the parameters AUCL and CPEAK must be within the 90% confidence interval of 80 to 125% of the corresponding values for the branded product STALEVO® for therapeutic equivalence, i.e., an acceptable bioavailability. The data presented in Table 3 show AUCL and CPEAK have 90% confidence intervals that are within the acceptable range of 80-125% of STALEVO for each formulation tested and for each of carbidopa, levodopa, and entacapone.

TABLE 2

|  | AUCL (ng · hr/ml) (% CV) | 90% CI | CPEAK (ng/ml) (% CV) | 90% CI | TPEAK (hr) (% CV) |
|---|---|---|---|---|---|
| Bioavailability of carbidopa | | | | | |
| Stable pharmaceutical dosage form (50 mg/200 mg/200 mg) | 946.2 (39.47%) | 91-105% | 178.0 (42.99%) | 89-102% | 3.79 (27.81%) |
| STALEVO ® (50 mg/200 mg/200 mg) | 955.3 (37.28%) | | 182.9 (39.37%) | | 3.76 (26.64%) |
| Stable pharmaceutical dosage form (12.5 mg/50 mg/200 mg) | 232.1 | 89-109% | 48.6 | 87-104% | 2.93 |
| STALEVO ® (12.5 mg/50 mg/200 mg) | 227.5 | | 49.9 | | 3.03 |
| Bioavailability of levodopa | | | | | |
| Stable pharmaceutical dosage form (50 mg/200 mg/200 mg) | 5727.6 (29.63%) | 95-103% | 1514.9 (31.01%) | 89-100% | 2.08 (57.88%) |
| STALEVO ® (50 mg/200 mg/200 mg) | 5742.1 (27.99%) | | 1594.5 (24.57%) | | 2.17 (54.05%) |
| Stable pharmaceutical dosage form (12.5 mg/50 mg/200 mg) | 1076.2 | 102-111% | 463.7 | 99-111% | 1.24 |
| STALEVO ® (12.5 mg/50 mg/200 mg) | 1015.4 | | 445.0 | | 1.33 |
| Bioavailability of entacapone | | | | | |
| Stable pharmaceutical dosage form (50 mg/200 mg/200 mg) | 1576.3 (26.47%) | 92-100% | 1108.1 (49.99%) | 82-111% | 2.08 (78.61%) |
| STALEVO ® (50 mg/200 mg/200 mg) | 1641.9 (27.57%) | | 1136.4 (46.20%) | | 1.68 (85.33%) |
| Stable pharmaceutical dosage form (12.5 mg/50 mg/200 mg) | 1455.5 | 101-115% | 1188.7 | 96-122% | 1.78 |
| STALEVO ® (12.5 mg/50 mg/200 mg) | 1371.5 | | 1097.9 | | 1.45 |

Using a range of 80-125% of the pharmacokinetic parameters for STALEVO® the stable pharmaceutical dosage form has the following range of pharmacokinetic parameters:

TABLE 3

|  | AUCL (ng · hr/ml) | CPEAK (ng/ml) |
|---|---|---|
| Bioavailability of carbidopa | | |
| Stable pharmaceutical dosage form (50 mg/200 mg) | 764.2-1194.1 | 146.3-184.2 |
| Stable pharmaceutical dosage form (12.5 mg/50 mg/200 mg) | 182.0-284.4 | 40.0-62.5 |
| Bioavailability of levodopa | | |
| Stable pharmaceutical dosage form (50 mg/200 mg/200 mg) | 4593.7-7177.6 | 1275.6-1993.1 |
| Stable pharmaceutical dosage form (12.5 mg/50 mg/200 mg) | 812.3-1269.2 | 356.0-556.2 |
| Bioavailability of entacapone | | |
| Stable pharmaceutical dosage form (50 mg/200 mg/200 mg) | 1313.5-2052.4 | 909.1-1420.5 |
| Stable pharmaceutical dosage form (12.5 mg/50 mg/200 mg) | 1097.2-1714.4 | 878.3-1372.4 |

Although the various embodiments have been described in detail with particular reference to certain aspects thereof, it should be understood that the stable pharmaceutical dosage form is capable of other embodiments and its details are capable of modifications in various obvious respects. As is readily apparent to those skilled in the art, variations and modifications can be affected while remaining within the spirit and scope of the disclosed stable pharmaceutical dosage form. Accordingly, the foregoing disclosure, description, and figures are for illustrative purposes only and do not in any way limit the disclosed stable pharmaceutical dosage form, which is defined only by the claims.

What is claimed is:

1. A process for preparing a stable pharmaceutical dosage form comprising:
   a. mixing carbidopa, levodopa, and entacapone, or pharmaceutically acceptable salts, solvates, or hydrates thereof, and an optional first excipient to form a first mixture;
   b. granulating the first mixture with a granulation solution to form a granulation mixture;
   c. drying the granulation mixture to form dried granules comprising carbidopa, levodopa, and entacapone, or pharmaceutically acceptable salts, solvates, or hydrates thereof;
   d. combining the dried granules with at least one second excipient to form a second mixture; and
   e. compressing the second mixture into said stable pharmaceutical dosage form;
   wherein the pharmaceutical dosage form is stable when exposed to atmospheric conditions of 40° C. and 75% relative humidity.

2. The process of claim 1, wherein the first excipient is a starch selected from the group consisting of pregelatinized starch, corn starch, and a mixture thereof.

3. The process of claim 1, wherein the at least one second excipient is selected from the group consisting of microcrystalline cellulose, crospovidone, croscarmellose sodium, magnesium stearate, and a mixture thereof.

4. A stable pharmaceutical dosage form prepared by the process of claim 1 comprising combinations of carbidopa, levodopa, entacapone, and salts thereof selected from the group consisting of: 12.5 mg of carbidopa, 50 mg of levodopa, and 200 mg of entacapone; 18.75 mg of carbidopa, 75 mg of levodopa, and 200 mg of entacapone; 25 mg of carbidopa, 100 mg of levodopa, and 200 mg of entacapone; 31.25 mg of carbidopa, 125 mg of levodopa, and 200 mg of entacapone; 37.5 mg of carbidopa, 150 mg of levodopa, and 200 mg of entacapone; and 50 mg of carbidopa, 200 mg of levodopa, and 200 mg of entacapone.

5. A stable pharmaceutical dosage form prepared by the process of claim 3, wherein the dosage form exhibits a bioavailability substantially similar to the bioavailability of a reference dosage form that includes carbidopa, levodopa, and entacapone, wherein the reference dosage form does not include microcrystalline cellulose, and wherein the reference dosage form is prepared by separating a substantial portion of the carbidopa from the entacapone and levodopa.

6. A stable pharmaceutical dosage form prepared by a process comprising:
   a. mixing carbidopa, levodopa, and entacapone, or pharmaceutically acceptable salts, solvates, or hydrates thereof, and an optional first excipient to form a first mixture;
   b. granulating the first mixture with a granulation solution to form a granulation mixture;
   c. drying the granulation mixture to form dried granules comprising carbidopa, levodopa, and entacapone, or pharmaceutically acceptable salts, solvates, or hydrates thereof;
   d. combining the dried granules with at least one second excipient to form a second mixture; and
   e. compressing the second mixture into the stable pharmaceutical dosage form;
   wherein the pharmaceutical dosage form is stable when exposed to atmospheric conditions of 40° C. and 75% relative humidity.

7. The stable pharmaceutical dosage form of claim 6, wherein the stable pharmaceutical dosage form exhibits a bioavailability substantially similar to the bioavailability of a reference dosage form that includes carbidopa, levodopa, and entacapone, wherein the reference dosage form does not include microcrystalline cellulose, and wherein the reference dosage form is prepared by separating a substantial portion of the carbidopa from the entacapone and the levodopa.

8. The stable pharmaceutical dosage form of claim 6, wherein:
   the stable dosage form comprises 50 mg carbidopa, 200 mg levodopa, and 200 mg entacapone; and
   the stable dosage form exhibits the following pharmacokinetic parameters:

|  | AUCL (ng · hr/ml) | CPEAK (ng/ml) |
|---|---|---|
| Bioavailability of carbidopa | | |
| 50 mg carbidopa/ 200 mg levodopa/ 200 mg entacapone | 764.2-1194.1 | 146.3-184.2 |
| Bioavailability of levodopa | | |
| 50 mg carbidopa/ 200 mg levodopa/ 200 mg entacapone | 4593.7-7177.6 | 1150-1993.1 |
| Bioavailability of entacapone | | |
| 50 mg carbidopa/ 200 mg levodopa/ 200 mg entacapone | 1313.5-2052.4 | 690-1420.5. |

9. The stable pharmaceutical dosage form of claim 6, wherein:
the stable dosage form comprises 12.5 mg carbidopa, 50 mg levodopa, and 200 mg entacapone; and
the stable dosage form exhibits the following pharmacokinetic parameters:

|  | AUCL (ng · hr/ml) | CPEAK (ng/ml) |
|---|---|---|
| Bioavailability of carbidopa | | |
| 12.5 mg carbidopa/ 50 mg levodopa/ 200 mg entacapone | 182.0-284.4 | 40.0-62.5 |
| Bioavailability of levodopa | | |
| 12.5 mg carbidopa/ 50 mg levodopa/ 200 mg entacapone | 812.3-1269.2 | 356.0-556.2 |
| Bioavailability of entacapone | | |
| 12.5 mg carbidopa/ 50 mg levodopa/ 200 mg entacapone | 1097.2-1714.4 | 660-1372.4. |

10. The stable pharmaceutical dosage form of claim 6, wherein amounts by weight of each of methyl-Dopa (L-tyrosine, 3-hydroxy-α-methyl-, sesquihydrate), 3,4 DHPA (3,4-dihydroxyphenylacetone), Imp A (3,4-dihydroxy-5-nitrobenzaldehyde), Imp B (N,N'-diethyl-2-cyanoacetamide), Imp C (3,4-dihydroxy-5-nitrobenzoic acid), Imp H ((Z)-2-cyano-3-(3,4-dihydroxy-5-nitrobenzoic acid)), and other impurities derived from entacapone, carbidopa, and/or levodopa do not significantly increase upon storage for up to 24 weeks at 40° C. and 75% relative humidity.

11. The stable pharmaceutical dosage form of claim 6, wherein the stable pharmaceutical dosage form meets at least one of the following conditions:
i. a concentration of methyl-Dopa (L-tyrosine, 3-hydroxy-α-methyl-, sesquihydrate) is less than or equal to about 0.22%, by weight, at the time of manufacture; less than or equal to about 0.23%, by weight, after 8 weeks of storage at 40° C. and 75% relative humidity; or less than or equal to about 0.24%, by weight, after 12 weeks of storage at 40° C. and 75% relative humidity;
ii. a concentration of 3,4-DHPA (3,4-dihydroxyphenylacetone) is less than or equal to about 0.13%, by weight, at the time of manufacture; less than or equal to about 0.23%, by weight, after 8 weeks of storage at 40° C. and 75% relative humidity; or less than or equal to about 0.27% by weight after 12 weeks of storage at 40° C. and 75% relative humidity;
iii. a concentration of carbidopa- or levodopa- derived impurities other than methyl-Dopa and 3,4-DHPA is less than or equal to about 0.05%, by weight, at the time of manufacture or less than or equal to about 0.05%, by weight, after 4, 8, or 12 weeks of storage at 40° C. and 75% relative humidity;
iv. a concentration of Imp A (3,4-dihydroxy-5-nitrobenzaldehyde), Imp B (N,N'-diethyl-2-cyanoacetamide), Imp C (3,4-dihydroxy-5-nitrobenzoic acid), Imp H ((Z)-2-cyano-3-(3,4-dihydroxy-5-nitrobenzoic acid)) are each less than or equal to about 0.05%, by weight, at the time of manufacture or less than or equal to about 0.05%, by weight, after 4, 8, or 12 weeks of storage at 40° C. and 75% relative humidity;
v. a concentration of any impurity derived from entacapone, other than Imp A, Imp B, Imp C, and Imp H, is less than or equal to about 0.06% at the time of manufacture or less than or equal to about 0.06%, by weight, after 4, 8, or 12 weeks of storage at 40° C. and 75% relative humidity.

12. The stable pharmaceutical dosage form of claim 6, wherein the first excipient is a starch selected from the group consisting of pregelatinized starch, corn starch, and a mixture thereof.

13. The stable pharmaceutical dosage form of claim 6, wherein the at least one second excipient is selected from the group consisting of microcrystalline cellulose, crospovidone, croscarmellose sodium, magnesium stearate, and a mixture thereof.

14. The stable pharmaceutical dosage form of claim 6, wherein the dosage form exhibits a bioavailability substantially similar to the bioavailability of a reference dosage form that includes carbidopa, levodopa, and entacapone, wherein the reference dosage form does not include microcrystalline cellulose, and wherein the reference dosage form is prepared by separating a substantial portion of the carbidopa from the entacapone and levodopa.

15. A stable pharmaceutical dosage form comprising a mixture of entacapone, carbidopa, levodopa, or salts thereof, and microcrystalline cellulose;
wherein amounts by weight of each of methyl-Dopa (L-tyrosine, 3-hydroxy-α-methyl-, sesquihydrate), 3,4-DHPA (3,4-Dihydroxyphenylacetone), Imp A (3,4-dihydroxy-5-nitrobenzaldehyde), Imp B (N,N'-diethyl-2-cyanoacetamide), Imp C (3,4-dihydroxy-5-nitrobenzoic acid), and Imp H ((Z)-2-cyano-3-(3,4-dihydroxy-5-nitrobenzoic acid)), do not significantly increase upon storage for up to 12 weeks at 40° C. and 75% relative humidity.

16. The stable pharmaceutical dosage form of claim 15, wherein:
the stable dosage form comprises 50 mg carbidopa, 200 mg levodopa, and 200 mg entacapone; and
the stable dosage form exhibits the following pharmacokinetic parameters:

|  | AUCL (ng · hr/ml) | CPEAK (ng/ml) |
|---|---|---|
| Bioavailability of carbidopa | | |
| 50 mg carbidopa/ 200 mg levodopa/ 200 mg entacapone | 764.2-1194.1 | 146.3-184.2 |
| Bioavailability of levodopa | | |
| 50 mg carbidopa/ 200 mg levodopa/ 200 mg entacapone | 4593.7-7177.6 | 1150-1993.1 |
| Bioavailability of entacapone | | |
| 50 mg carbidopa/ 200 mg levodopa/ 200 mg entacapone | 1313.5-2052.4 | 690-1420.5. |

17. The stable pharmaceutical dosage form of claim 15, wherein:
the stable dosage form comprises 12.5 mg carbidopa, 50 mg levodopa, and 200 mg entacapone; and the stable dosage form exhibits the following pharmacokinetic parameters:

|  | AUCL (ng · hr/ml) | CPEAK (ng/ml) |
|---|---|---|
| Bioavailability of carbidopa | | |
| 12.5 mg carbidopa/<br>50 mg levodopa/<br>200 mg entacapone | 182.0-284.4 | 40.0-62.5 |
| Bioavailability of levodopa | | |
| 12.5 mg carbidopa/<br>50 mg levodopa/<br>200 mg entacapone | 812.3-1269.2 | 356.0-556.2 |
| Bioavailability of entacapone | | |
| 12.5 mg carbidopa/<br>50 mg levodopa/<br>200 mg entacapone | 1097.2-1714.4 | 660-1372.4. |

18. The stable pharmaceutical dosage form of claim 15, wherein the stable pharmaceutical dosage form meets at least one of the following conditions:
   i. a concentration of methyl-Dopa (L-tyrosine, 3-hydroxy-α-methyl-, sesquihydrate) is less than or equal to about 0.22%, by weight, at the time of manufacture; less than or equal to about 0.23%, by weight, after 8 weeks of storage at 40° C. and 75% relative humidity; or less than or equal to about 0.24%, by weight, after 12 weeks of storage at 40° C. and 75% relative humidity;
   ii. a concentration of 3,4-DHPA (3,4-dihydroxyphenylacetone) is less than or equal to about 0.13%, by weight, at the time of manufacture; less than or equal to about 0.23%, by weight, after 8 weeks of storage at 40° C. and 75% relative humidity; or less than or equal to about 0.27% by weight after 12 weeks of storage at 40° C. and 75% relative humidity;
   iii. a concentration of carbidopa- or levodopa- derived impurities other than methyl-Dopa and 3,4-DHPA is less than or equal to about 0.05%, by weight, at the time of manufacture or less than or equal to about 0.05%, by weight, after 4, 8, or 12 weeks of storage at 40° C. and 75% relative humidity;
   iv. a concentration of Imp A (3,4-dihydroxy-5-nitrobenzaldehyde), Imp B (N,N'-diethyl-2-cyanoacetamide), Imp C (3,4-dihydroxy-5-nitrobenzoic acid), Imp H ((Z)-2-cyano-3-(3,4-dihydroxy-5-nitrobenzoic acid)) are each less than or equal to about 0.05%, by weight, at the time of manufacture or less than or equal to about 0.05%, by weight, after 4, 8, or 12 weeks of storage at 40° C. and 75% relative humidity;
   v. a concentration of any impurity derived from entacapone, other than Imp A, Imp B, Imp C, and Imp H, is less than or equal to about 0.06% at the time of manufacture or less than or equal to about 0.06%, by weight, after 4, 8, or 12 weeks of storage at 40° C. and 75% relative humidity.

19. The stable pharmaceutical dosage form of claim 15, further comprising an excipient selected from the group consisting of a starch, crospovidone, croscarmellose sodium, magnesium stearate, and a combination thereof.

* * * * *